US011100782B2

(12) United States Patent
Roxas (10) Patent No.: US 11,100,782 B2
(45) Date of Patent: Aug. 24, 2021

(54) SYSTEM AND METHODS FOR REMOTE UPDATES ON MEDICAL DEVICES (71) Applicant: Fenwal, Inc., Lake Zurich, IL (US)

(72) Inventor: James D. Roxas, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 16/658,383

(22) Filed: Oct. 21, 2019

(65) Prior Publication Data
US 2020/0160686 A1 May 21, 2020

Related U.S. Application Data (60) Provisional application No. 62/767,873, filed on Nov. 15, 2018.

(51) Int. Cl.
G08B 21/04 (2006.01)
G16H 40/67 (2018.01)
H04W 4/80 (2018.01)
A61M 1/34 (2006.01)
G08B 3/10 (2006.01)

(52) U.S. Cl.
CPC ....... G08B 21/0453 (2013.01); A61M 1/3496 (2013.01); G08B 3/10 (2013.01); G16H 40/67 (2018.01); H04W 4/80 (2018.02); A61M 2205/18 (2013.01); A61M 2205/3553 (2013.01); A61M 2205/3561 (2013.01); A61M 2205/3584 (2013.01)

(58) Field of Classification Search
CPC ...... G08B 21/0453; G08B 3/10; G16H 40/67; H04W 4/80; A61M 1/3496; A61M 2205/18; A61M 2205/3553; A61M 2205/3561; A61M 2205/3584; A61B 5/0002
USPC .......................... 340/539.1, 539.12, 539.13, 340/539.11–539.19
See application file for complete search history.

(56) References Cited

U.S. PATENT DOCUMENTS 6,790,198 B1  9/2004  White et al.
8,646,695 B2  2/2014  Worrall et al.
9,314,159 B2  4/2016  Lyon et al.
2005/0143671 A1  6/2005  Hastings et al.
(Continued)

OTHER PUBLICATIONS

European Patent Office, extended European Search Report, counterpart EP Appl. No. 19206231, dated Apr. 14, 2020.
(Continued)

*Primary Examiner* — Emily C Terrell
(74) *Attorney, Agent, or Firm* — Cook Alex Ltd.

(57) ABSTRACT

A system for providing remote updates on medical devices includes a wireless communication network, a wearable update output device comprising a wireless receiver in wireless communication with the wireless communication network, and a medical system comprising a medical device, an update generator, and a wireless transmitter. The update generator is configured to monitor a process carried out using the medical device, to generate one or more updates according to device states that occur during the process, and to route the updates to the wireless transmitter. The network is in wireless communication with the wireless transmitter, and is configured to route updates received from the wireless transmitter to the wireless receiver of the wearable update output device.

20 Claims, 2 Drawing Sheets (56) References Cited

U.S. PATENT DOCUMENTS

| | | | |
|---|---|---|---|
| 2008/0194925 A1* | 8/2008 | Alsafadi | A61B 5/411 600/301 |
| 2009/0069785 A1* | 3/2009 | Miller | A61M 5/14244 604/500 |
| 2011/0001605 A1* | 1/2011 | Kiani | G16H 40/00 340/5.6 |
| 2013/0072765 A1* | 3/2013 | Kahn | G06F 1/3206 600/301 |
| 2013/0157571 A1 | 6/2013 | Wondka et al. | |
| 2013/0283256 A1* | 10/2013 | Proud | G08C 17/02 717/172 |
| 2017/0128668 A1* | 5/2017 | Miller | A61M 5/14244 |
| 2017/0249831 A1* | 8/2017 | Wengrovitz | H04W 76/12 |
| 2018/0360675 A1* | 12/2018 | Darrah | A61G 1/06 |
| 2019/0385744 A1* | 12/2019 | Freeman | A61B 5/7267 |

OTHER PUBLICATIONS

Wilson, M., A Disney MagicBand for Hospitals, Fast Company (Jan. 29, 2015) (4 pages).
Williams, M., A Disney MagicBand . . . For Hospitals?, HEROX—The Exponent (circa Jan. 2015) (4 pages).

\* cited by examiner

SYSTEM AND METHODS FOR REMOTE UPDATES ON MEDICAL DEVICES

CROSS-REFERENCE TO RELATED APPLICATIONS

This application claims the benefit of U.S. Provisional Patent App. No. 62/767,873, filed Nov. 15, 2018, which is expressly incorporated herein by reference in its entirety.

TECHNICAL FIELD

The present disclosure is generally directed to systems and methods for remote updates on medical devices, and in particular to systems and methods that provide remote updates on various states (e.g., alarm states) of medical devices.

BACKGROUND

Even in their earliest forms, medical devices, such as infusion pumps and apheresis machines, provided some type of visual and audible alert to healthcare providers and/or patients as to certain device states. These alerts often included a flashing light and a single tone or multi-tone alarm, for example. The device would generate such an alert to indicate that the line connected to the patient had become occluded, or that the fluid remaining in the container or bag connected to the patient was running low. In fact, as medical devices became smarter, with larger and more sophisticated on-board controllers or processors, the number and types of alerts that the device was capable of providing increased.

It is not necessarily the case that such an alert will require immediate intervention by a healthcare profession or the patient, however. In fact, the devices may time the generation of the alert so that the healthcare profession has a suitable amount of time to address the issue before the issue becomes a significant concern or risk. For example, where the alert may be associated with an infusion process, and specifically the state where the fluid level is running low in the source (e.g., bag) for that infusion process, the alert may be provided 15 or 20 minutes before the device (e.g., pump) will fully exhaust the fluid in the bag.

Unfortunately, the meaning and timing of such alerts is not always obvious to the patient or donor, and his or her friends and family. The patient or donor and his or her friends and family may have little or no prior exposure to the medical device in question. The patient, donor, or their friends and family may become alarmed or agitated when an alert is provided, because they may assume a worst case scenario—a failure of the machine that will lead to risk or injury to the patient or donor. Where the patient is receiving a treatment from the medical device or is donating biological fluids (e.g., blood), this agitation may have an impact on the quality of the treatment received by the patient or the quantity of the fluid received from the donor.

Given the number of alerts that may be provided, it is not reasonable to expect a healthcare professional to be able to explain to a patient or donor every alert that may be occurring during a treatment or process. Not only is it unlikely that a patient would remember all of the possible alerts, the patient may become focused only on those alerts that are associated with significant issues, even when the signals associated with such an alert may be confused with the signals for other less significant alerts. Neither is it possible to simply deactivate the alerts, because the alerts do provide valuable, even critical, information to the healthcare professional.

SUMMARY

In a first aspect of the disclosure, a system for providing remote updates on medical devices includes a wireless communication network, a wearable update output device comprising a wireless receiver in wireless communication with the wireless communication network, and a medical system comprising a medical device, an update generator, and a wireless transmitter. The update generator is configured to monitor a process carried out using the medical device, to generate one or more updates according to device states that occur during the process, and to route the updates to the wireless transmitter. The network is in wireless communication with the wireless transmitter, and is configured to route updates received from the wireless transmitter to the wireless receiver of the wearable update output device.

In a second aspect, a system for providing remote updates on medical devices includes a wearable update output device comprising a wireless receiver, and a medical system comprising a medical device, an update generator, and a wireless transmitter. The update generator is configured to monitor a process carried out using the medical device, to generate one or more updates according to device states that occur during the process, and to route the updates to the wireless transmitter. The wireless receiver is in wireless communication with the wireless transmitter to receive updates transmitted by the wireless transmitter.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
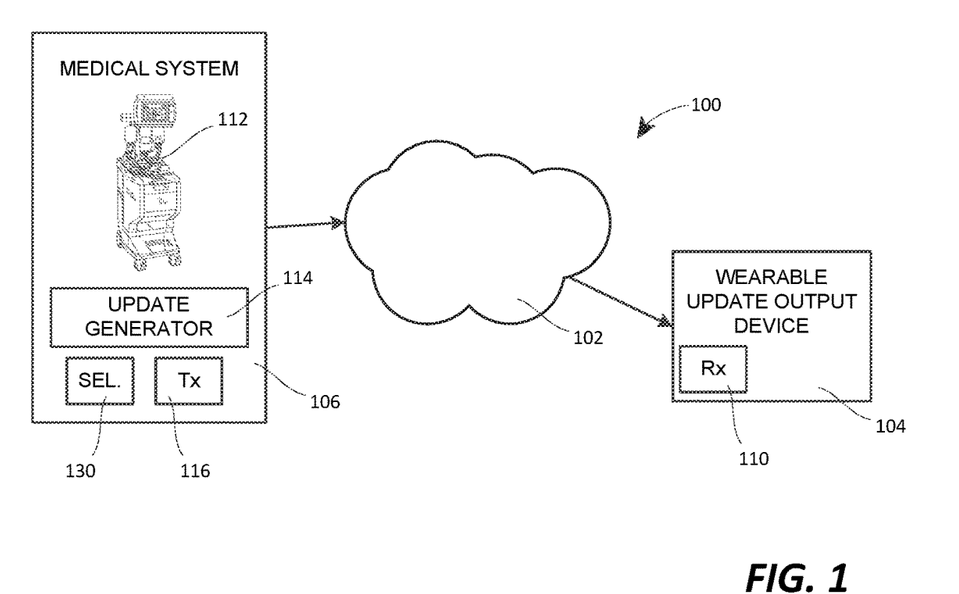
FIG. 1 is a diagram of an embodiment of a system for remote updates on medical devices.

Turning first to FIG. 1, a system 100 for providing remote updates on medical devices includes a wireless communication network 102, a wearable update output device 104 (e.g., a wristband or a badge that can be attached to the user's clothing), and a medical system 106. According to certain embodiments, the wireless communication network 102 may include only elements of the wearable update output device 104 and the medical system 106, and the wearable update output device 104 may be in direct wireless communication with the medical system 106 (e.g., a wireless receiver of the wearable update output device 104 may be in wireless communication with a wireless transmitter of the medical system 106). According to other embodiments, the wireless communication network 102 may include a plurality of devices, some of which communicate wirelessly with the wearable update output device 104 and/or with the medical system 106 (connection points), and some of which may communicate over hardwired or wireless communication connections between those connection points to facilitate wireless communication between the output device 104 and with the medical system 106.

As illustrated, the wearable update output device 104 includes a wireless receiver 110 in wireless communication with the wireless communication network 102. The medical system 106 includes a medical device 112 (e.g., an apheresis separator), an update generator 114, and a wireless transmitter 116. The update generator 114 is configured to monitor a process carried out using the medical device 112, to generate one or more updates according to device states that occur during the process, and to route the updates to the wireless transmitter 116. The network 102 is in wireless communication with the wireless transmitter 116 and is configured to route updates received from the wireless transmitter 116 to the wireless receiver 110 of the wearable update output device 104.

In operation, the medical device 112 may achieve a particular device state during a process. For example, where the medical device 112 is biological fluid processing equipment that may include a reusable separator, or processor, and a disposable set, or fluid circuit, the device 112 may have a device state that occurs when the disposable set has been primed with fluid. The update generator 114 may generate an update regarding that device state, forward the update to the transmitter 116, which transmits the update to the wireless communication network that routes the update to the wearable update output device 104. As a further example, device 112 may have a fault state where the device 112 determines that an occlusion has occurred in one of the lines of the set. In such a situation, the update generator 114 would generate an update regarding that device state, forward the update to the transmitter 116, which transmits the update to the wireless communication network that routes the update to the wearable update output device 104.

In either setting, it is important to note that the update generated by the update generator 114 does not include information regarding a patient or donor that may be associated with the medical device 112. The update involves the device state, and while the update may be associated with information regarding the device 112 to permit identification of the device 112 when a plurality of devices 112 are in communication with a single wearable update output device 104, the updates will not include information regarding the patient. As such, privacy and security concerns relating to the storage and transmission of confidential patient information are not implicated by the generation and transmission of the updates within the system 100.

Furthermore, in this embodiment, where there is one-way communication between the medical device 112 and the wearable update output device 104, there is no concern for improper commands to be received from devices other than the wearable update output device 104, because the system 100 does not provide for control of the device 112 from a remote location. According to other embodiments, however, two-way communication between the medical device 112 and the wearable update output device 104 may be provided.

For example, the wireless transmitter 116 may be a wireless transceiver, and the wireless receiver 110 may be a wireless transceiver. Further, the wearable update output device 104 may be configured to generate a command and route the command to the wireless transceiver 110 of the wearable update output device 104. Further, the network 102 may be configured to route updates received from the wireless transceiver 110 of the wearable update output device 104 to the medical device 112 via the wireless transceiver 116 of the medical system 106.

According to such an embodiment, it may be desirable to have a further level of security added to the communications between the wearable update output device 104 and the medical system 106. For example, the medical system 106 may require a password or passcode to be provided by the user or operator of the wearable update output device 104 along with the command. The medical system 106 may compare the password or passcode to a list of passwords or passcodes (maintained at the medical system 106, or at a remote server accessible by the medical system 106 over the wireless network 102, for example), and only act on the command received from the wearable update output device 104 (e.g., pass the command to the medical device 112) if the password or passcode matches one of the passwords or passcodes on the list.

Figure 2:
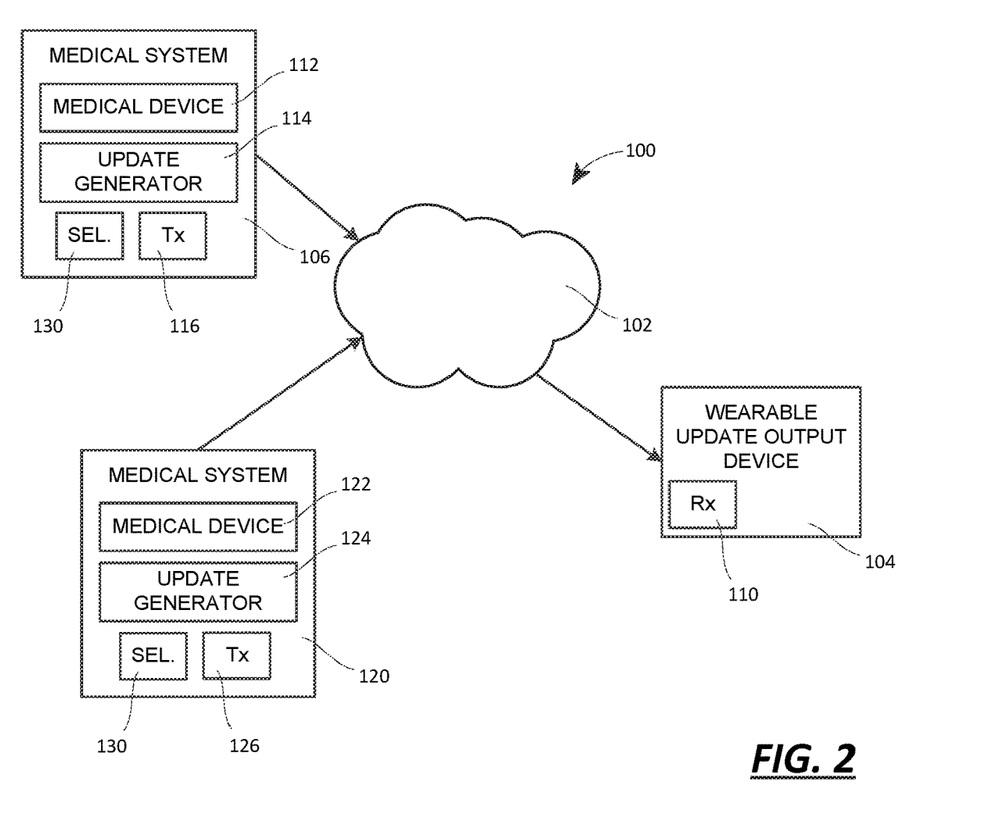
FIG. 2 is a diagram of another embodiment of a system for remote updates on medical devices.

While the embodiment of FIG. 1 includes a single medical system 106 in wireless communication with the wearable update output device 104, the system 100 is not so limited in all embodiments. For example, the system 100 may include at least one additional medical system 120, as illustrated in FIG. 2. While the embodiment of the system 100 of FIG. 2 includes only two medical systems 106, 120, it will be recognized that the system 100 could include many more (e.g., 5, 10, 15 or more) medical systems, all in communication with one (or more) wearable update output device(s) 104.

The at least one additional medical device 120 may include a medical device 122, an update generator 124, and a wireless transmitter 126. The update generator 124 of the at least one additional medical system 122 may be configured to monitor a process carried out using the medical device 122, to generate one or more updates according to device states that occur during the process, and to route the updates to the wireless transmitter 126. The network 102 may be in wireless communication with the wireless transmitter 126 of the at least one additional medical system 122 and configured to route updates received from the wireless transmitter 126 of the at least one additional medical system 122 to the wireless receiver 110 of the wearable update output device 104, along with the updates received from the wireless transmitter 116.

According to an alternate embodiment, the medical system may include multiple medical devices connected or coupled to a single update generator and a single transmitter. It will be recognized that according to such an embodiment, the update generator would be configured to monitor processes carried out using any of the connected or coupled medical devices, to generate one or more updates according to device states that occur during those processes, and to route the updates to the wireless transmitter. The wireless transmitter would then transmit the updates to the wireless communication network, which would then route the updates to the wearable update output device(s).

In either setting, the wearable update output device 104 may be configured with additional abilities to handle the routing of updates from the systems 106, 120, or more particularly from the devices 112, 122. For example, the wearable update output device 104 may be configured to permit the updates to be sorted and ordered according to manual selections or automatically. This is explained in detail below.

In any of the embodiments discussed relative to FIGS. 1 and 2, the medical system 106 may include an alarm selector 130, the alarm selector 130 configured to silence alarms generated by the medical device 112. According to certain embodiments, the alarm selector 130 is configured to automatically silence alarms generated by the medical device 112 if the update generator 114, 124 has been activated. In this fashion, the updates provided to the wearable update output device 104 may alert the responsible healthcare profession to the need to a state of the medical device 112, 122 without the alarms being activated, which may cause the patient or donor connected to the medical device 112, 122 to become agitated or frightened.

Thus, an embodiment of a system 100 for remote updates of medical devices may provide one or more of the following advantages. The system permits a user to monitor a medical device remotely, which permits the user to attend to other activities while continuing to be aware of the devices operational states. In fact, the system permits the user potentially to monitor multiple medical devices at the same time. According to certain embodiments, the system may also provide for the user to remotely control the medical device(s). Further, the system permits the user to monitor the medical device(s) without alarms being displayed to a patient or donor that is connected to the medical device(s), limiting or eliminating the patient's or donor's exposure to these alarms. Also, because the information being communicated relates to the device, and not the patient, privacy and security concerns relative to patient information may be limited or eliminated.

Figure 3:
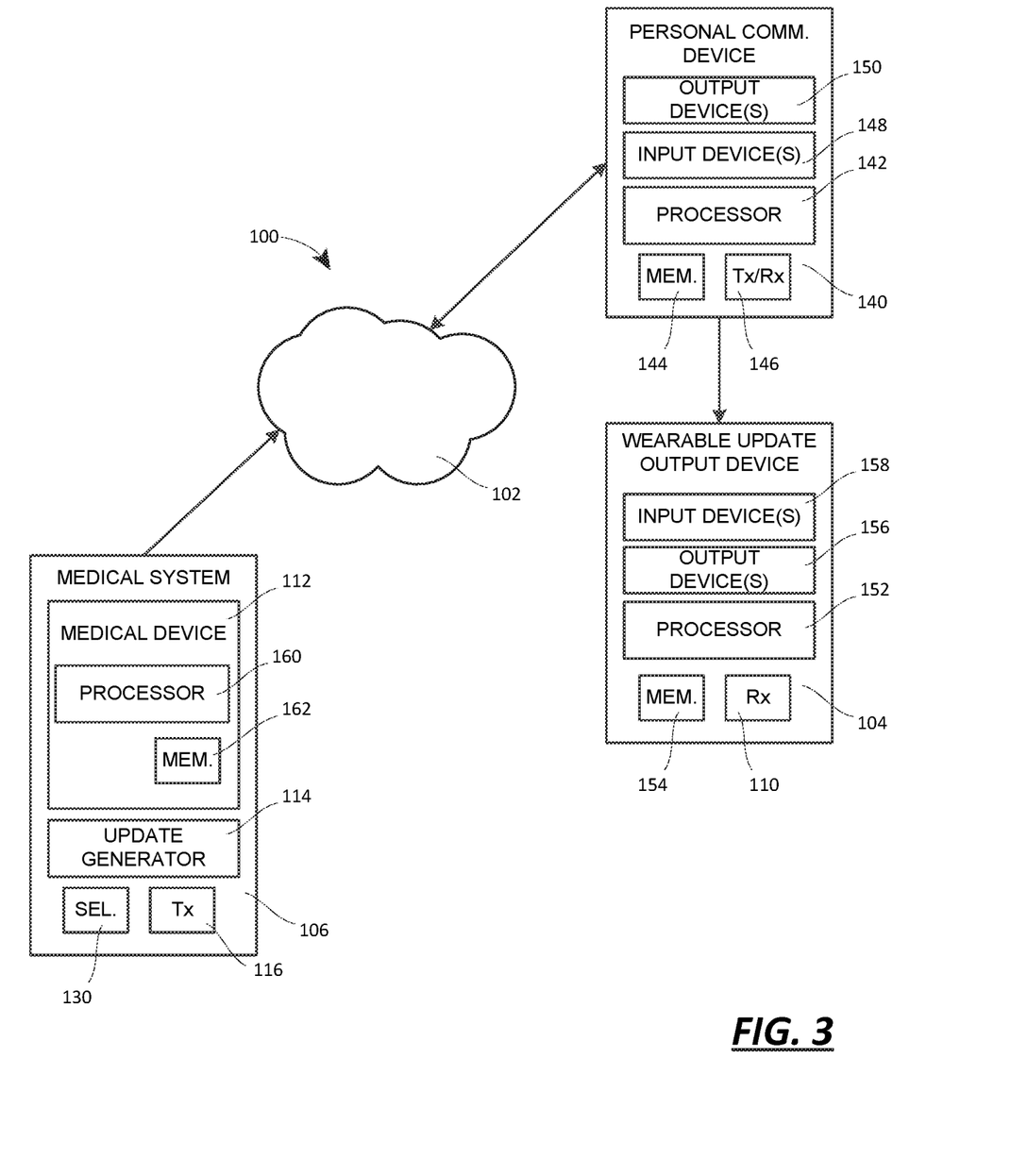
FIG. 3 is a diagram of a further embodiment of a system for remote updates on medical devices.

Having discussed the structure and operation of various embodiments of the system 100 in general terms, the details of the aspects of the system 100 are now discussed, with reference to FIG. 3.

To begin, the wireless communication network 102 may be a communication network configured in the form of a wireless local area network, such as a WI-FI network. As such, the network may include equipment, such as wireless routers and repeaters, and even servers. The network may also include personal communication devices 140, such as personal computers or personal mobile devices (e.g., smartphones), that are capable of wireless connection with the other components of the wireless communication network 102. These personal communication devices 140, as well as other equipment that makes up the wireless communication network 102, may be capable of two-way communication even if the medical system 106, 120 and wearable update output device 104 are capable of only one-way communication.

As illustrated, the personal communication device 140 may include a one or more processors 142, memory 144, one or more wireless transceivers 146, input devices (e.g., buttons, keyboard, point device, touch screen, etc.) 148 and output devices 150 (e.g., touch screen, speakers, etc.). The memory 144 may include one or more tangible non-transitory computer readable memories, having computer executable instructions stored thereon. The processor 142 may carry out instructions stored in the memory 144 so that the processor 142 operates according to the present disclosure. For example, the processor 142 may be configured (or programmed) to control one of the transceivers 146 to form a wireless personal area network with the wearable update output device 104. According to certain embodiments, the wireless personal area network may operate according to the BLUETOOTH standard. All of these components may be disposed on or in a housing, such as a hand-held, portable housing.

In the same fashion, the wearable update output device 104 may include one or more processors 152, memory 154, the wireless receiver 110, and at least output devices 156.

The memory 154 may include one or more tangible non-transitory computer readable memories, having computer executable instructions stored thereon. The processor 152 may carry out instructions stored in the memory 154 so that the processor 152 operates according to the present disclosure. The type and sophistication of the output device 156 may vary, but may include at least one of an audio output device (e.g., speaker), a visual output device (e.g., display), and a haptic output device (e.g., vibrator), and the wearable update output device 104, and more particularly the processor 152, may be configured (or programmed) to activate the at least one of the audio output device, the visual output device, and the haptic output device when updates are received. All of these components may be disposed on or in the wearable frame, which may be a wristband or a badge that may be attached to the user's clothing, for example.

According to one embodiment, the wearable update output device 104 may be in the form of a wristband, and the output device 156 may include a haptic output device in the form of a vibrator. The purpose of such an embodiment of the output device 156 would be to alert the healthcare professional that an update has been received. This might be useful where only one type of update (e.g., an alarm) is to be received by the wearable update output device 104.

According to a more sophisticated embodiment, the output device 156 may be in the form of or may include a visual output, in the form of a display, such as an LCD or LED display. Such an output device 156 may provide the capability of providing an alphanumeric message to the healthcare professional. For example, the output device 156 may provide a scrolling message that includes an identifier (e.g., number) for the medical device 112, 122, along with an identifier (e.g., number or phrase) for the update. According to such an embodiment, it may even be possible to receive numerous updates, and to include all of the updates in a rolling message on the output device.

According to other embodiments, it may be possible to have more than one type of output device 156. These multiple types of output device 156 also may be used in concert with each other. For example, the wearable update output device 104 may include a haptic output device to get the wearer's attention, and a visual output device to provide more detailed information regarding the update once the attention has been attracted.

According to a further embodiment, the output device 156 on the wearable update output device 104 may be used to attract the wearer's attention, and then the output device 150 associated with a personal communication device 140 may be used to communicate further information to the wearer. In this fashion, the size and complexity of the wearable update output device 104 may be minimized by taking advantage of the greater sophistication of the personal communication device 140.

According to those embodiments where the wearable update output device 104 is in two-way communication with the medical system 106, 120 (for example, by being in two-way communication with the personal communication device 140), the wearable update output device 104 may also include an input device or devices 158. The input device(s) 158 may be used to provide a command to the wearable update output device 104, which is then transmitted via the personal communication device 140 and the network 102 to the medical system 106, 120, for the medical device 122 to carry out. As an alternative, the input device 158 may be used to order the updates being received from the medical systems 106, 120.

That is, according to those embodiments of the system 100 where the wearable update output device 104 is configured to receive updates from the medical system 106 and updates from the at least one additional medical system 120, the wearable update output device 104 may be configured (e.g., the processor 152 may be programmed) to prioritize the updates from the medical system 106 and the updates from the at least one additional medical system 120. For example, prioritization may include ranking the updates from the medical system 106 and the updates from the at least one additional medical system 120, either relative to updates received from that system 106, 120 or relative to all updates received from all systems 106, 120.

According to certain embodiments, the wearable update output device 104 may be configured to automatically prioritize the updates from the medical system 106 and the updates from the at least one additional medical system 120 according to a rules set. For example, the rules set may require that the highest priority be associated with updates from either system 106, 120 that involve a risk to the health of the patient or donor. The lowest priority may be associated with updates from either system 106, 120 that involve routine measurement checks or tests. The rules set could also weight events from certain systems 106, 120 relative to other systems 106, 120, such that an event from the system 106, for example, is given a higher priority than the systems from other systems, like the system 120.

Alternatively, the wearable update output device 104 may be configured to prioritize the updates from the medical system 106 and the updates from the at least one additional medical system 120 according to a command received from the input device 158. For example, where all of the updates are related to operational issues that do not involve risk to the health of the patient, the healthcare provider may organize the list of updates according to the amount of time it will likely take to resolve the issue, or according to whether the update requires immediate intervention or intervention within a certain amount of time. IN such a circumstance, the user may use the input device 158 (e.g., a touch display) to order the updates displayed on the output device 156 (e.g., the touch display).

Other output devices may exhibit greater levels of sophistication relative to the activities that can be carried out via the wearable update output device 104, such as forwarding updates to the personal communication device 140 or a remote computer or server for inclusion in a daily, weekly or monthly report. It may also be possible to have the wearable update output device 104 configured (e.g., the processor programmed) to schedule maintenance tasks and/or to route those maintenance tasks to other persons connected to the wireless network 102, or to use the wireless network 102 to route those tasks to other persons connected to other networks (e.g., the Internet). Depending on the sophistication of the wearable update output device 104, a greater degree of cooperation between the wearable update output device 104 and the personal communication device 140 may occur, permitting certain tasks to be carried out by the personal communication device 140 instead of the wearable update output device 104.

As will be recognized in FIG. 3, the medical device 112 (like the wearable update output device 104 and the personal communication device 140) may include a processor 160 and a memory 162, the memory 162 including one or more tangible non-transitory computer readable memories, having computer executable instructions stored thereon, which instructions the processor 160 may carry out so that the processor 160 operates according to the present disclosure. For example, where the medical device 112 is a pump, the processor 160 and memory 162 may be in the form of a pump controller. The processor 160 may be programmed to cause the hardware of the medical device 112 (e.g., clamp(s), pump(s), centrifuge, spinning membrane, etc.) to carry out the process that is monitored by the update generator 114, the states of which cause the generator 114 to generate the updates that are transmitted by the transmitter 116 to the wireless network 102 and routed to the wearable update output device 104.

According to certain embodiments, the controller including the processor 160 and memory 162 to be configured (e.g., the processor 160 to be programmed) as the update generator 114. That is, the processor 160 may be programmed to control the hardware of the medical device 112 to carry out the process that is monitored and to generate the updates that are transmitted by the transmitter 116 to the wireless network 102 and routed to the wearable update output device 104. In such an embodiment, certain equipment (e.g., the processor 160) may be shared by the medical device 112 and the update generator 114, while also defining, in part, the medical device 112 and the update generator 114.

Thus, an improved method and system for addressing medical device updates has been disclosed. The description provided above is intended for illustrative purposes, and is not intended to limit the scope of the disclosure to any particular method, system, apparatus or device described herein Other Aspects Aspect 1. A system for providing remote updates on medical devices, the system comprising:
a wireless communication network;
a wearable update output device comprising a wireless receiver in wireless communication with the wireless communication network; and
a medical system comprising a medical device, an update generator, and a wireless transmitter,
the update generator configured to monitor a process carried out using the medical device, to generate one or more updates according to device states that occur during the process, and to route the updates to the wireless transmitter;
the network in wireless communication with the wireless transmitter and configured to route updates received from the wireless transmitter to the wireless receiver of the wearable update output device.

Aspect 2. The system according to aspect 1, wherein
the wireless transmitter comprises a wireless transceiver,
the wireless receiver comprises a wireless transceiver,
the wearable update output device is configured to generate a command and route the command to the wireless transceiver of the wearable update output device, and
the network is configured to route updates received from the wireless transceiver of the wearable update output device to the medical device via the wireless transceiver of the medical system.

Aspect 3. The system according to aspect 1 or 2, wherein the wireless communication network comprises a wireless personal communication device, the wireless personal communication device in wireless communication with the wearable update output device.

Aspect 4. The system according to aspect 3, wherein the wireless communication network comprises a wireless personal area network, and the wireless personal communication device and the wearable update output device communicate over a wireless personal area network.

Aspect 5. The system according to any of the preceding aspects, further comprising:

at least one additional medical system comprising a medical device, an update generator, and a wireless transmitter, the update generator of the at least one additional medical system configured to monitor a process carried out using the medical device of the at least one additional medical system, to generate one or more updates according to device states that occur during the process, and to route the updates to the wireless transmitter of the at least one additional medical system, the network coupled to the wireless transmitter of the at least one additional medical system and configured to route updates received from the wireless transmitter of the at least one additional medical system to the wireless receiver of the wearable update output device.

Aspect 6. The system according to aspect 5, wherein the wearable update output device is configured to receive updates from the medical system and updates from the at least one additional medical system, and to prioritize the updates from the medical system and the updates from the at least one additional medical system.

Aspect 7. The system according to aspect 6, wherein prioritization comprises ranking the updates from the medical system and the updates from the at least one additional medical system.

Aspect 8. The system according to aspect 6 or 7, wherein the wearable update output device is configured to automatically prioritize the updates from the medical system and the updates from the at least one additional medical system according to a rules set.

Aspect 9. The system according to aspect 6 or 7, wherein the wearable update output device comprises an input device, and the wearable update output device is configured to prioritize the updates from the medical system and the updates from the at least one additional medical system according to an command received from the input device.

Aspect 10. The system according to any one of the preceding aspects, wherein the wearable update output device comprises at least one of an audio output device, a visual output device, and a haptic output device, and the wearable update output device is configured to activate the at least one of the audio output device, the visual output device, and the haptic output device when updates are received Aspect 11. The system according to any one of the preceding aspects, wherein the medical device comprises a medical device controller and the medical device controller is configured as the update generator.

Aspect 12. The system according to any one of the preceding aspects, wherein the medical system comprises an alarm selector, the alarm selector configured to silence alarms generated by the medical device.

Aspect 13. The system according to aspect 12, wherein the alarm selector is configured to automatically silence alarms generated by the medical device if the update generator has been activated.

Aspect 14. A system for providing remote updates on medical devices, the system comprising:

a wearable update output device comprising a wireless receiver; and a medical system comprising a medical device, an update generator, and a wireless transmitter, the update generator configured to monitor a process carried out using the medical device, to generate one or more updates according to device states that occur during the process, and to route the updates to the wireless transmitter;

the wireless receiver in wireless communication with the wireless transmitter.

Aspect 15. The system according to aspect 14, wherein the medical device comprises a medical device controller, and the medical device controller is configured as the update generator.

Aspect 16. The system according to aspect 14 or 15, wherein the medical system comprises an alarm selector, the alarm selector configured to silence alarms generated by the medical device.

Aspect 17. The system according to aspect 16, wherein the alarm selector is configured to automatically silence alarms generated by the medical device if the update generator has been activated.

The invention claimed is:

1. A system for providing remote updates on medical devices, the system comprising:
   a wireless communication network;
   a wearable update output device comprising a wireless receiver in wireless communication with the wireless communication network; and
   a medical system comprising a medical device including a reusable separator and a disposable fluid circuit, an update generator, and a wireless transmitter,
   the update generator configured to monitor a process carried out using the reusable separator and the disposable fluid circuit of the medical device, to generate one or more updates according to device states that occur during the process using the reusable separator and the disposable fluid circuit, and to route the updates to the wireless transmitter,
   wherein the one or more updates do not include information regarding a patient or donor associated with the medical device;
   the network in wireless communication with the wireless transmitter and configured to route updates received from the wireless transmitter to the wireless receiver of the wearable update output device.

2. The system according to claim 1, wherein
   the wireless transmitter comprises a wireless transceiver,
   the wireless receiver comprises a wireless transceiver,
   the wearable update output device is configured to generate a command and route the command to the wireless transceiver of the wearable update output device, and
   the network is configured to route the command received from the wireless transceiver of the wearable update output device to the medical device via the wireless transceiver of the medical system.

3. The system according to claim 1, wherein the wireless communication network comprises a wireless personal communication device, the wireless personal communication device in wireless communication with the wearable update output device.

4. The system according to claim 3, wherein the wireless communication network comprises a wireless personal area network, and the wireless personal communication device and the wearable update output device communicate over a wireless personal area network.

5. The system according to claim 1, further comprising
at least one additional medical system comprising a medical device including a reusable separator and a disposable fluid circuit, an update generator, and a wireless transmitter,
the update generator of the at least one additional medical system configured to monitor a process carried out using the reusable separator and the disposable fluid circuit of the medical device of the at least one additional medical system, to generate one or more updates according to device states that occur during the process using the reusable separator and the disposable fluid circuit, and to route the updates to the wireless transmitter of the at least one additional medical system,
wherein the one or more updates do not include information regarding a patient or donor associated with the medical device of the at least one additional medical system,
the network coupled to the wireless transmitter of the at least one additional medical system and configured to route updates received from the wireless transmitter of the at least one additional medical system to the wireless receiver of the wearable update output device.

6. The system according to claim 5, wherein the wearable update output device is configured to receive updates from the medical system and updates from the at least one additional medical system, and to prioritize the updates from the medical system and the updates from the at least one additional medical system.

7. The system according to claim 6, wherein prioritization comprises ranking the updates from the medical system and the updates from the at least one additional medical system.

8. The system according to claim 6, wherein the wearable update output device is configured to automatically prioritize the updates from the medical system and the updates from the at least one additional medical system according to a rules set.

9. The system according to claim 6, wherein the wearable update output device comprises an input device, and the wearable update output device is configured to prioritize the updates from the medical system and the updates from the at least one additional medical system according to a command received from the input device.

10. The system according to claim 1, wherein the wearable update output device comprises at least one of an audio output device, a visual output device, and a haptic output device, and the wearable update output device is configured to activate the at least one of the audio output device, the visual output device, and the haptic output device when updates are received.

11. The system according to claim 1, wherein the medical device comprises a medical device controller and the medical device controller is configured as the update generator.

12. The system according to claim 1, wherein the medical system comprises an alarm selector, the alarm selector configured to silence alarms generated by the medical device.

13. The system according to claim 12, wherein the alarm selector is configured to automatically silence alarms generated by the medical device if the update generator has been activated.

14. A system for providing remote updates on medical devices, the system comprising:
a wearable update output device comprising a wireless receiver; and
a medical system comprising a medical device including a reusable separator and a disposable fluid circuit, an update generator, and a wireless transmitter,
the update generator configured to monitor a process carried out using the reusable separator and the disposable fluid circuit of the medical device, to generate one or more updates according to device states that occur during the process using the reusable separator and the disposable fluid circuit, and to route the updates to the wireless transmitter,
wherein the one or more updates do not include information regarding a patient or donor associated with the medical device;
the wireless receiver in wireless communication with the wireless transmitter to receive updates transmitted by the wireless transmitter.

15. The system according to claim 14, wherein the medical device comprises a medical device controller, and the medical device controller is configured as the update generator.

16. The system according to claim 14, wherein the medical system comprises an alarm selector, the alarm selector configured to silence alarms generated by the medical device.

17. The system according to claim 16, wherein the alarm selector is configured to automatically silence alarms generated by the medical device if the update generator has been activated.

18. The system according to claim 1, wherein the one or more updates include a device state of the medical device, wherein the device state is one of an operational state and a fault state.

19. A system for providing remote updates on medical devices, the system comprising:
a wireless communication network;
a wearable update output device comprising a wireless receiver in wireless communication with the wireless communication network; and
a medical system comprising a medical device, an update generator, and a wireless transmitter,
the update generator configured to monitor a process carried out using the medical device, to generate one or more updates according to device states that occur during the process, and to route the updates to the wireless transmitter,
wherein the one or more updates do not include information regarding a patient or donor associated with the medical device,
the network in wireless communication with the wireless transmitter and configured to route updates received from the wireless transmitter to the wireless receiver of the wearable update output device,
wherein the one or more updates include a device state of the medical device, wherein the device state is one of an operational state and a fault state, and
wherein the device states include one or more of:
a state wherein a disposable set has been primed with fluid;
a state wherein an occlusion has occurred in a line of the disposable set; and
a state wherein a fluid level in a source bag is running low.

20. A system for providing remote updates on medical devices, the system comprising:
a wearable update output device comprising a wireless receiver; and
a medical system comprising a medical device, an update generator, and a wireless transmitter, the update generator configured to monitor a process carried out using the medical device, to generate one or more updates according to device states that occur during the process, and to route the updates to the wireless transmitter, wherein the one or more updates do not include information regarding a patient or donor associated with the medical device, the wireless receiver in wireless communication with the wireless transmitter to receive updates transmitted by the wireless transmitter, wherein the one or more updates include a device state of the medical device, wherein the device state is one of an operational state and a fault state, and the device states include one or more of:

a state wherein a disposable set has been primed with fluid;

a state wherein an occlusion has occurred in a line of the disposable set; and a state wherein a fluid level in a source bag is running low.

* * * * *